US00PP13184P2

(12) United States Plant Patent
Harkness et al.

(10) Patent No.: US PP13,184 P2
(45) Date of Patent: Nov. 5, 2002

(54) FLORIBUNDA ROSE PLANT NAMED 'HARBADGE'

(75) Inventors: Philip A. Harkness, Hitchin (GB); Robert B. Harkness, Mougins (FR)

(73) Assignee: Jackson & Perkins Wholesale, Inc., Medford, OR (US)

( * ) Notice: Subject to any disclaimer, the term of this patent is extended or adjusted under 35 U.S.C. 154(b) by 26 days.

(21) Appl. No.: 09/686,529

(22) Filed: Oct. 10, 2000

(51) Int. Cl.[7] ..... A01H 5/00
(52) U.S. Cl. ..... Plt./141
(58) Field of Search ..... Plt./133, 134

*Primary Examiner*—Bruce R. Campell
*Assistant Examiner*—Susan B. McCormick
(74) *Attorney, Agent, or Firm*—Klarquist Sparkman, LLP

(57) ABSTRACT

Floribunda rose plant having a compact, rounded, well-branched plant; fragrant blooms of many petals and a full, old-fashioned form; and dark green, glossy, disease resistant foliage.

1 Drawing Sheet

The present invention relates to a new and distinct variety of rose plant of the floribunda class which was originated by us by crossing the variety HARroony (U.S. Plant Pat. No. 5,582) with the variety HARwanted, (not patented).

The primary objective of this breeding was to produce a new rose variety having a compact, rounded, well branched plant; blooms that have many petals and full, old fashioned form; dark green, disease resistant foliage; and flowers with fragrance. The objective was substantially achieved, along with other desirable improvements, as evidenced by the following unique combination of characteristics that are outstanding in the new variety and that distinguish it from its parents, as well as from all other varieties of which we are aware:

1. Strong fragrance.
2. Rounded, upright, well branched growth habit;
3. Old fashioned flower form;
4. Dark green, glossy foliage; and
5. Resistance to rust and powdery mildew.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of our new rose cultivar with color descriptions using terminology in accordance with The Royal Horticultural Society (London) Colour Chart (1966), except where ordinary dictionary significance of color is indicated.

Parentage:
*Seed parent.*—HARroony (U.S. Plant Pat. No. 5,582).
*Pollen parent.*—HARwanted (Not patented).

Classification:
*Botanical.*—*Rosa hybrida.*
*Commercial.*—Floribunda.

FLOWER

Observations made from specimens grown in a garden environment at Somis, Calif., and two years of age in January, 1999, to July, 2000.

Blooming habit: Continuous.

Bud:

*Size.*—One and a quarter inches long and 3½ inches in diameter at the base when the petals start to unfurl.

*Form.*—The bud form is short, pointed ovoid.

*Color.*—When sepals first divide, bud color is Yellow-Whitish Group 158B. When half blown, the upper sides of the petals are Yellow-White Group 158C; and the lower sides of the petals are Yellow-White Group 158C.

*Sepals.*—Color: Green Group 138B with a blush of Red Group 46D on areas exposed to bright sunlight. Surface texture: Covered in fine hairs. Length: 15/16 inch–1⅛ inch. Width: ⅜ inch–½ inch. There are three normally to heavily appendaged sepals. There are two unappendaged sepals with hairy edges.

*Receptacle.*—Color: Yellow-Green Group 146C. Shape: Funnel. Size: Medium, about ⅜ inch×5/16 inch. Surface: Smooth.

*Peduncle.*—Length: Short, averaging about 1½ inches to 2 inches. Surface: Smooth, with some small glands. Color: Yellow-Green Group 146C. Strength: Stiff, erect.

Bloom:

*Size.*—Medium. Average open size is 3½ inches.

*Borne.*—Several together in flat clusters to blooms.

*Stems.*—Strength Strong. Average length is about 12 to 16 inches.

*Form.*—When first open: Bloom is globular. Permanence: Flattens, all petals curl.

*Petalage.*—Number of petals under normal conditions: 40.

*Color.*—The upper sides of the petals are Yellow-White Group 158C. The reverse sides of the petals are Yellow-White Group 158C. The base of each petal has a small 3/16 inch×3/16 inch Yellow Group 11C color spot on both petal surfaces. The major color on the upper side is Yellow-White Group 158C.

*Variegations.*—None.

*Discoloration.*—The general tonality at the end of the first day: No change. At the end of the third day: No change.

*Fragrance.*—Strong, fruity.

Petals:

*Texture.*—Thick, smooth and leathery.

*Shape.*—Round to deltoid.

*Base.*—Cuneate.

*Apex.*—Obtuse.

*Form.*—Tips slightly recurved.

*Arrangement.*—Imbricated. Petaloids in the center range from one to seven in ten flowers observed and are Yellow-White Group 158C in color and ¼ inch×⅛ inch to ½ inch×¼ inch in size.

*Persistence.*—Petals drop off cleanly before drying.

*Lastingness.*—On the plant: Fair (about 5–6 days). As a cut flower: Fair (about 6–7 days).

Reproductive parts:

*Anthers.*—Size: Length: 1/16 inch–⅛ inch. Quantity: 120–150. Color: Yellow-Orange Group 22C. Arrangement: Regular around styles, mixed with petaloids.

*Filaments.*—Color: Yellow Group 2C. Length: 3/16–¼ inch.

*Pollen.*—Color: Yellow-Orange Group 22B.

*Pistils.*—Number: 90–110.

*Styles.*—Color: Red Group 45C. Length: 3/16 inch–¼ inch.

*Stigmas.*—Color: Greyed-Yellow Group 162C. Length: 1/16 inch.

*Hips.*—None observed.

Plant:

*Form.*—Bush.

*Growth.*—Vigorous, upright, branching and compact. At maturity, height is 3½ feet, width is 3 feet.

Foliage: Number of leaflets on normal mid-stem leaves: 5 or 7.

*Size.*—Large (6½ inches long×4 inches wide).

*Quantity.*—Abundant.

*Color.*—New foliage: Upper surface: Greyed-Red Group 178A. Lower surface: Greyed-Red Group 178B. Old foliage: Upper surface: Green Group 139A. Lower surface: Green Group 137C.

Leaflets:

*Size.*—Length: 2 inches. Width: 1 inch.

*Shape.*—Pointed oval.

*Texture.*—Leathery, glossy.

*Edge.*—Serrated.

*Serration.*—Single, small.

*Venation pattern.*—Costate.

*Vein color.*—Lower surface: Green Group 137C.

*Petiole rachis.*—Color: Green Group 137D with the upper surface also with a caste of Greyed-Purple Group 183C, especially at the leaflet axils.

*Petiole underside.*—Smooth with occasional prickles.

*Stipules.*—Medium (about ½ inch to ⅝ inch), bearded and edged on glands.

*Disease resistance.*—Resistant to mildew and rust, susceptible to blackspot under normal growing conditions.

Wood:

*New wood.*—Color: Yellow-Green Group 146D. Bark: Smooth.

*Old wood.*—Color: Green Group 137D. Bark: Smooth.

Prickles:

*Quantity.*—On main canes from base: 22–24 per six inches of stem. On laterals from main canes: 22–24 per six inches of stem.

*Form.*—Medium, hooked slightly downward.

*Color when young.*—Greyed-Red Group 182B.

*Color when mature.*—Greyed-Orange Group 177B.

*Size.*—Length: ⅜ inch.

Small prickles:

*Quantity.*—On main stalks: Few. On laterals: Few.

*Color.*—Young: Greyed-Red Group 182B. Mature: Greyed-Orange Group 177B.

We claim:

1. A new and distinct variety of rose plant of the floribunda class, substantially as herein shown and described, characterized particularly by having a compact, rounded, well-branched plant; fragrant blooms of many petals and a full, old fashioned form; and dark green, glossy, disease resistant foliage.

* * * * *

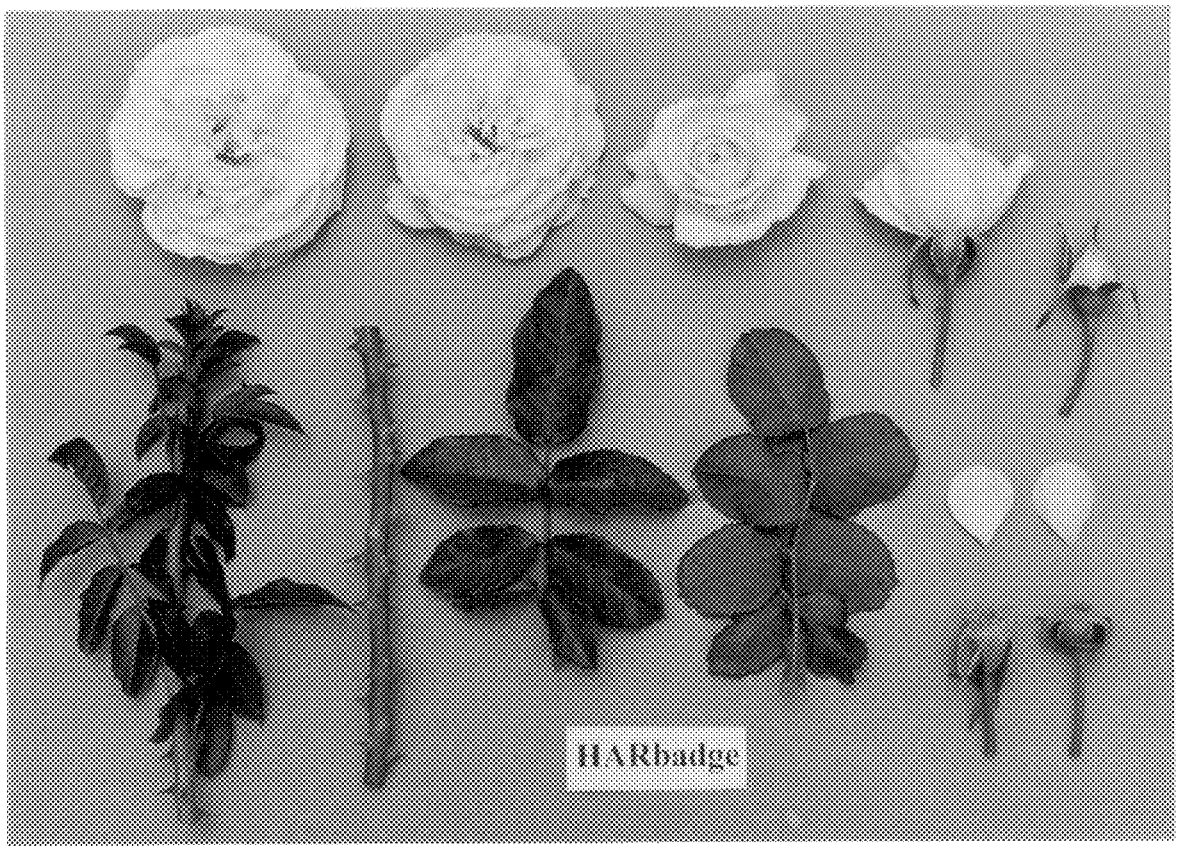
HARbadge